United States Patent [19]

Dahl et al.

[11] Patent Number: 5,164,404
[45] Date of Patent: Nov. 17, 1992

[54] HYDRAZONE DERIVATIVES AND THEIR USE

[75] Inventors: Bjarne H. Dahl; Frank Wätjen, both of Copenhagen, Denmark

[73] Assignee: NeuroSearch A/S, Glostrup, Denmark

[21] Appl. No.: 670,061

[22] Filed: Mar. 15, 1991

[51] Int. Cl.$^5$ .................. A61K 31/44; A61K 31/40; C07D 209/56; C07D 213/34

[52] U.S. Cl. .................. 514/339; 514/411; 514/418; 546/273; 548/450

[58] Field of Search .............. 546/273; 548/450; 514/339, 411, 418

[56] References Cited

U.S. PATENT DOCUMENTS 4,780,477 10/1988 Kobayashi et al. .............. 514/418
4,988,710 1/1991 Olney .............................. 548/419

FOREIGN PATENT DOCUMENTS 0205299 12/1986 European Pat. Off. .

OTHER PUBLICATIONS

Chemical Abstracts: CA 52: 11014–11015a.
J. Martinet, Ann. Chim. (Paris), 9(11), 96–97 (1919).
J. Martinet, C. R. Hebd, Seances Acad. Sci., 166, 851–853.
W. Calvert et al., J. Amer. Chem. Soc., 80, 962–964.
Hinsberg, Chem. Ber., 21, 110–119 (1888).
J. Martinet, C. R.: Hebd, Seances Acad. Sci., 168, 689–691.
S. Swarup et al., Indian Drugs, 27(11), 563–567 (1990).
F. D. Popp, J. Med. Chem., 13(5), 1017–1018 (1970).
S. Agarwal, Indian Drugs, 22(12), 633–639 (1985).
F. D. Popp, J. Heterocyclic Chem., 21(6), 1641–1645 (1984).
Copy of CAS On-Line File Registry for the compound 109725-61-3.
Copy of Beilstein On-Line Search Report for the CAS Registry number 109725-61-3 compound.

Primary Examiner—Joseph Paul Brust
Assistant Examiner—MarySusan H. Gabilan
Attorney, Agent, or Firm—Gordon W. Hueschen

[57] ABSTRACT

A method of antagonizing the biological effects of an excitatory amino acid of a subject in need of such antagonization, comprising the step of administering to said subject an effective excitatory amino acid antagonizing amount of an indole-2,3-dione-3-hydrazone derivative, is disclosed. Certain of the compounds are novel. The compounds and pharmaceutical compositions containing the compounds are useful in the treatment of central nervous system disorders and especially conditions sensitive to excitatory amino acids.

12 Claims, No Drawings

HYDRAZONE DERIVATIVES AND THEIR USE

The present invention relates to a method of treatment with compounds having excitatory amino acid antagonizing properties, pharmaceutical compositions comprising such compounds, novel compounds having excitatory amino acid antagonizing properties and to the preparation of such compounds.

It is an object of the present invention to provide a method of treating diseases in mammals, including a human, by antagonizing an excitatory amino acid in such mammal.

A second object of the present invention is to provide novel pharmaceutical compositions useful for the treatment of diseases in mammals, including a human, acting by antagonizing an excitatory amino acid in such mammal.

A third object of the present invention is to provide novel compounds useful for the treatment of diseases in mammals, including a human, acting by antagonizing an excitatory amino acid in such mammal.

SUMMARY OF THE INVENTION

The invention then, inter alia, comprises the following, alone or in combination:

A method of antagonizing the biological effects of an excitatory amino acid of a subject in need of such antagonization comprising the step of administering to said subject an effective excitatory amino acid antagonizing amount of an indole-2,3-dione-3-hydrazone compound having the formula

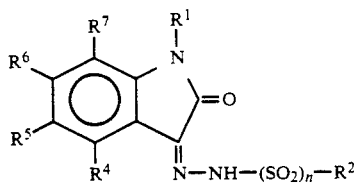

wherein
n is 0 or 1;
$R^1$ is hydrogen, $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;
$R^2$ is pyridyl or phenyl, both of which may be substituted one or more times preferably in the ortho and para positions with halogen, $CF_3$, $NO_2$, $CN$, phenyl, or $SO_2NR''R'''$ wherein $R''$ and $R'''$ independently are hydrogen, benzyl, or $C_{1-6}$-alkyl;
$R^4$, $R^5$, $R^6$, $R^7$ independently are hydrogen, $C_{1-6}$-alkyl which may be branched, phenyl, halogen, $C_{1-6}$-alkoxy, $NO_2$, $CN$, $CF_3$, or $SO_2NR^{11}R^{12}$ wherein $R^{11}$ and $R^{12}$ independently are hydrogen, benzyl, or $C_{1-6}$-alkyl; or $R^6$ and $R^7$ together form an additional 4 to 8 membered carbocyclic ring which may be aromatic or partial saturated and which may be substituted with halogen, $NO_2$, $CF_3$, $CN$, $SO_2NR^{13}R^{14}$ wherein $R^{13}$ and $R^{14}$ independently are hydrogen, benzyl, or $C_{1-6}$-alkyl, and $R^4$ and $R^5$ have the meanings set forth above;
or $R^4$ and $R^5$ together form an additional 4 to 8 membered carbocyclic ring which may be aromatic or partial saturated and which may be substituted with halogen, $NO_2$, $CF_3$, $CN$, $SO_2NR^{13}R^{14}$ wherein $R^{13}$ and $R^{14}$ independently are hydrogen, benzyl, or $C_{1-6}$-alkyl, and $R^6$ and $R^7$ have the meanings set forth above;
a method as above wherein at least one of $R^4$, $R^5$, $R^6$ or $R^7$ is an electron withdrawing substituent such as $NO_2$, $CF_3$, $CN$, $SO_2NR^{11}R^{12}$, or halogen and $R^1$, $R^2$, $R^4$, $R^5$, $R^6$, $R^7$, $R^{11}$, and $R^{12}$ otherwise have the meanings set forth above,
a method as first above wherein $R^5$ is $NO_2$, F, $CF_3$, or CN,
moreover a method of antagonizing the biological effects of an excitatory amino acid as first above, wherein the compound is administered in the form of a pharmaceutical composition thereof, in which it is present together with a pharmaceutically acceptable carrier or diluent,
and a method of antagonizing the biological effects of an excitatory amino acid as second above, wherein the compound is administered in the form of a pharmaceutical composition thereof, in which it is present together with a pharmaceutically acceptable carrier or diluent,
further a pharmaceutical composition for use in antagonizing the biological effects of an excitatory amino acid of a subject in need of such antagonization comprising an effective excitatory amino acid antagonizing amount of a compound having the formula

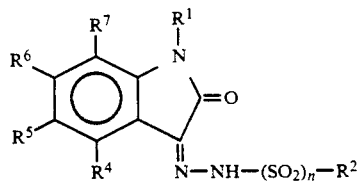

wherein
n is 0 or 1;
$R^1$ is hydrogen, $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;
$R^2$ is pyridyl or phenyl, both of which may be substituted one or more times preferably in the ortho and para positions with halogen, $CF_3$, $NO_2$, $CN$, phenyl, or $SO_2NR''R'''$ wherein $R''$ and $R'''$ independently are hydrogen, benzyl, or $C_{1-6}$-alkyl;
$R^4$, $R^5$ independently are hydrogen, $C_{1-6}$-alkyl which may be branched, phenyl, halogen, $C_{1-6}$-alkoxy, $NO_2$, $CN$, $CF_3$, or $SO_2NR^{11}R^{12}$ wherein $R^{11}$ and $R^{12}$ independently are hydrogen, benzyl, or $C_{1-6}$-alkyl; and $R^6$ and $R^7$ together form an additional 4 to 8 membered carbocyclic ring which may be aromatic or partial saturated and which may be substituted with halogen, $NO_2$, $CF_3$, $CN$, $SO_2NR^{13}R^{14}$ wherein $R^{13}$ and $R^{14}$ independently are hydrogen, benzyl, or $C_{1-6}$-alkyl;
or $R^6$, $R^7$ independently are hydrogen, $C_{1-6}$-alkyl which may be branched, phenyl, halogen, $C_{1-6}$-alkoxy, $NO_2$, $CN$, $CF_3$, or $SO_2NR^{11}R^{12}$ wherein $R^{11}$ and $R^{12}$ independently are hydrogen, benzyl, or $C_{1-6}$-alkyl; and $R^4$ and $R^5$ together form an additional 4 to 8 membered carbocyclic ring which may be aromatic or partial saturated and which may be substituted with halogen, NO$_2$, CF$_3$, CN, SO$_2$NR$^{13}$R$^{14}$ wherein R$^{13}$ and R$^{14}$ independently are hydrogen, benzyl, or C$_{1-6}$-alkyl;

and R$^1$, R$^4$ and R$^5$ are not all hydrogen when R$^2$ is unsubstituted phenyl and R$^6$ and R$^7$ together form an additional unsubstituted benzo ring, and method of antagonizing the biological effects of an excitatory amino acid of a subject in need thereof comprising the step of administering to said subject a pharmaceutical composition as above, further a compound having the formula

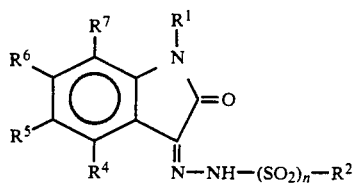

wherein
n is 0 or 1;
R$^1$ is hydrogen, C$_{1-6}$-alkyl which may be branched, C$_{3-7}$-cycloalkyl, benzyl, phenyl which may be substituted, acyl, hydroxy, C$_{1-6}$-alkoxy, CH$_2$CO$_2$R' wherein R' is hydrogen or C$_{1-6}$-alkyl which may be branched, CH$_2$CN, CH$_2$CONR$^{IV}$R$^V$ wherein R$^{IV}$ and R$^V$ independently are hydrogen or C$_{1-6}$-alkyl, or CH$_2$C(=NOH)NH$_2$;

R$^2$ is pyridyl or phenyl, both of which may be substituted one or more times preferably in the ortho and para positions with halogen, CF$_3$, NO$_2$, CN, phenyl, or SO$_2$NR''R''' wherein R'' and R''' independently are hydrogen, benzyl, or C$_{1-6}$-alkyl;

R$^4$, R$^5$ independently are hydrogen, C$_{1-6}$-alkyl which may be branched, phenyl, halogen, C$_{1-6}$-alkoxy, NO$_2$, CN, CF$_3$, or SO$_2$NR$^{11}$R$^{12}$ wherein R$^{11}$ and R$^{12}$ independently are hydrogen, benzyl, or C$_{1-6}$-alkyl;

and R$^6$ and R$^7$ together form an additional 4 to 8 membered carbocyclic ring which may be aromatic or partial saturated and which may be substituted with halogen, NO$_2$, CF$_3$, CN, SO$_2$NR$^{13}$R$^{14}$ wherein R$^{13}$ and R$^{14}$ independently are hydrogen, benzyl, or C$_{1-6}$-alkyl;

or R$^6$, R$^7$ independently are hydrogen, C$_{1-6}$-alkyl which may be branched, phenyl, halogen, C$_{1-6}$-alkoxy, NO$_2$, CN, CF$_3$, or SO$_2$NR$^{11}$R$^{12}$ wherein R$^{11}$ and R$^{12}$ independently are hydrogen, benzyl, or C$_{1-6}$-alkyl; and R$^4$ and R$^5$ together form an additional 4 to 8 membered carbocyclic ring which may be aromatic or partial saturated and which may be substituted with halogen, NO$_2$, CF$_3$, CN, SO$_2$NR$^{13}$R$^{14}$ wherein R$^{13}$ and R$^{14}$ independently are hydrogen, benzyl, or C$_{1-6}$-alkyl;

and a compound as above wherein the additional ring formed by R$^6$ and R$^7$ or R$^4$ and R$^5$ is substituted with halogen, NO$_2$, CF$_3$, CN or SO$_2$NR$^{13}$R$^{14}$ wherein R$^{13}$ and R$^{14}$ independently are hydrogen, benzyl, or C$_{1-6}$-alkyl, and a compound as above, which is 8-nitro-1H-4,5,6,7-tetrahydro-benz[e]indole-2,3-dione-3-(2-nitrophenylhydrazone), and a compound as above, which is 5-nitro-1H-6,7,8,9-tetrahydro-benz[g]indole-2,3-dione-3-phenylsulphonylhydrazone, and a compound as above, which is 5-nitro-1H-6,7,8,9-tetrahydro-benz[g]indole-2,3-dione-3-(2-pyridylhydrazone), further a method of preparing a compound having the formula

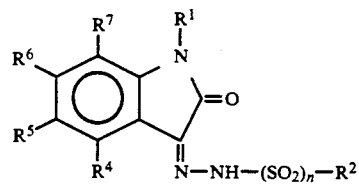

wherein
n is 0 or 1;
R$^1$ is hydrogen, C$_{1-6}$-alkyl which may be branched, C$_{3-7}$-cycloalkyl, benzyl, phenyl which may be substituted,
acyl, hydroxy, C$_{1-6}$-alkoxy, CH$_2$CO$_2$R' wherein R' is hydrogen or C$_{1-6}$-alkyl which may be branched, CH$_2$CN, CH$_2$CONR$^{IV}$R$^V$ wherein R$^{IV}$ and R$^V$ independently are hydrogen or C$_{1-6}$-alkyl, or CH$_2$C(=NOH)NH$_2$;

R$^2$ is pyridyl or phenyl, both of which may be substituted one or more times preferably in the ortho and para positions with halogen, CF$_3$, NO$_2$, CN, phenyl, or SO$_2$NR''R''' wherein R'' and R''' independently are hydrogen, benzyl, or C$_{1-6}$-alkyl;

R$^4$, R$^5$ independently are hydrogen, C$_{1-6}$-alkyl which may be branched, phenyl, halogen, C$_{1-6}$-alkoxy, NO$_2$, CN, CF$_3$, or SO$_2$NR$^{11}$R$^{12}$ wherein R$^{11}$ and R$^{12}$ independently are hydrogen, benzyl, or C$_{1-6}$-alkyl; and R$^6$ and R$^7$ together form an additional 4 to 8 membered carbocyclic ring which may be aromatic or partial saturated and which may be substituted with halogen, NO$_2$, CF$_3$, CN, SO$_2$NR$^{13}$R$^{14}$ wherein R$^{13}$ and R$^{14}$ independently are hydrogen, benzyl, or C$_{1-6}$-alkyl;

or R$^6$, R$^7$ independently are hydrogen, C$_{1-6}$-alkyl which may be branched, phenyl, halogen, C$_{1-6}$-alkoxy, NO$_2$, CN, CF$_3$, or SO$_2$NR$^{11}$R$^{12}$ wherein R$^{11}$ and R$^{12}$ independently are hydrogen, benzyl, or C$_{1-6}$-alkyl; and R$^4$ and R$^5$ together form an additional 4 to 8 membered carbocyclic ring which may be aromatic or partial saturated and which may be substituted with halogen, NO$_2$, CF$_3$, CN, SO$_2$NR$^{13}$R$^{14}$ wherein R$^{13}$ and R$^{14}$ independently are hydrogen, benzyl, or C$_{1-6}$-alkyl;

and R$^1$, R$^4$ and R$^5$ are not all hydrogen when R$^2$ is unsubstituted phenyl and R$^6$ and R$^7$ together form an additional unsubstituted benzo ring, comprising the step of reacting a compound of the formula

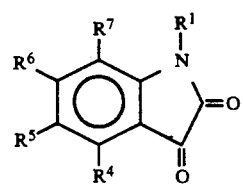

wherein $R^1$, $R^4$, $R^5$, $R^6$ and $R^7$ have the meanings set forth above, with a compound having the formula $H_2N-NH-(SO_2)_n-R^2$, wherein $R^2$ and $n$ have the meanings set forth above, and moreover the use of a compound having the formula

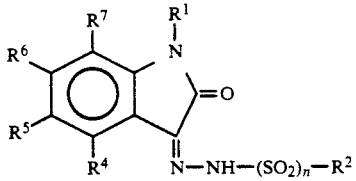

wherein
n is 0 or 1;
$R^1$ is hydrogen, $C_{1-6}$-alkyl which may be branched, $C_{3-7}$-cycloalkyl, benzyl, phenyl which may be substituted,
acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;
$R^2$ is pyridyl or phenyl, both of which may be substituted one or more times preferably in the ortho and para positions with halogen, $CF_3$, $NO_2$, $CN$, phenyl, or $SO_2NR''R'''$ wherein $R''$ and $R'''$ independently are hydrogen, benzyl, or $C_{1-6}$-alkyl;
$R^4$, $R^5$, $R^6$, $R^7$ independently are hydrogen, $C_{1-6}$-alkyl which may be branched, phenyl, halogen, $C_{1-6}$-alkoxy, $NO_2$, $CN$, $CF_3$, or $SO_2NR^{11}R^{12}$ wherein $R^{11}$ and $R^{12}$ independently are hydrogen, benzyl, or $C_{1-6}$-alkyl; or $R^6$ and $R^7$ together form an additional 4 to 8 membered carbocyclic ring which may be aromatic or partial saturated and which may be substituted with halogen, $NO_2$, $CF_3$, $CN$, $SO_2NR^{13}R^{14}$ wherein $R^{13}$ and $R^{14}$ independently are hydrogen, benzyl, or $C_{1-6}$-alkyl, and $R^4$ and $R^5$ have the meanings set forth above;
or $R^4$ and $R^5$ together form an additional 4 to 8 membered carbocyclic ring which may be aromatic or partial saturated and which may be substituted with halogen, $NO_2$, $CF_3$, $CN$, $SO_2NR^{13}R^{14}$ wherein $R^{13}$ and $R^{14}$ independently are hydrogen, benzyl, or $C_{1-6}$-alkyl, and $R^6$ and $R^7$ have the meanings set forth above;
and the use as above wherein at least one of $R^4$, $R^5$, $R^6$ or $R^7$ is an electron withdrawing substituent such as $NO_2$, $CF_3$, $CN$, $SO_2NR^{11}R^{12}$, or halogen and $R^1$, $R^2$, $R^4$, $R^5$, $R^6$, $R^7$, $R^{11}$ and $R^{12}$ otherwise have the meanings set forth above, and further a method of preparing a pharmaceutical preparation containing as active ingredient an effective amount of a compound having the formula

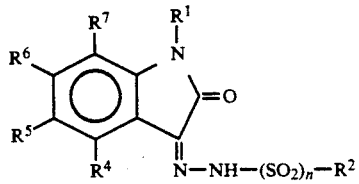

wherein
n is 0 or 1;

$R^1$ is hydrogen, $C_{1-6}$-alkyl which may be branched, $C_{3-7}$-cycloalkyl, benzyl, phenyl which may be substituted,
acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;
$R^2$ is pyridyl or phenyl, both of which may be substituted one or more times preferably in the ortho and para positions with halogen, $CF_3$, $NO_2$, $CN$, phenyl, or $SO_2NR''R'''$ wherein $R''$ and $R'''$ independently are hydrogen, benzyl, or $C_{1-6}$-alkyl;
$R^4$, $R^5$, $R^6$, $R^7$ independently are hydrogen, $C_{1-6}$-alkyl which may be branched, phenyl, halogen, $C_{1-6}$-alkoxy, $NO_2$, $CN$, $CF_3$, or $SO_2NR^{11}R^{12}$ wherein $R^{11}$ and $R^{12}$ independently are hydrogen, benzyl, or $C_{1-6}$-alkyl; or $R^6$ and $R^7$ together form an additional 4 to 8 membered carbocyclic ring which may be aromatic or partial saturated and which may be substituted with halogen, $NO_2$, $CF_3$, $CN$, $SO_2NR^{13}R^{14}$ wherein $R^{13}$ and $R^{14}$ independently are hydrogen, benzyl, or $C_{1-6}$-alkyl, and $R^4$ and $R^5$ have the meanings set forth above;
or $R^4$ and $R^5$ together form an additional 4 to 8 membered carbocyclic ring which may be aromatic or partial saturated and which may be substituted with halogen, $NO_2$, $CF_3$, $CN$, $SO_2NR^{13}R^{14}$ wherein $R^{13}$ and $R^{14}$ independently are hydrogen, benzyl, or $C_{1-6}$-alkyl, and $R^6$ and $R^7$ have the meanings set forth above.

Biological Activity

The compounds of the invention exhibit valuable biological properties because of their strong excitatory amino acid (EAA) (glycine, glutamate, quisqualate, ATPA ($\alpha$-amino-3-hydroxy-5-t-butylisoxazole-4-propionic acid), AMPA ($\alpha$-amino-3-hydroxy-5-methylisoxazole-4-propionic acid), kainate, NMDA (N-methyl-D-aspartate)) antagonizing properties.

Compounds of the invention show potent affinity for the glutamate subreceptor binding sites for kainate, NMDA, quisqualate and glycine. These properties make the compounds useful in the treatment of human malfunctions related to the excitatory amino acids (EAA).

Compounds of the invention exhibit binding at the $^3$H-kainate, NMDA, $^3$H-AMPA and/or $^3$H-glycine binding sites with $IC_{50}$ in the range of 1–100 $\mu$M. Examples of such compounds are for example
Z,E-1H-6,7,8,9-tetrahydro-benz[g]indole-2,3-dione-3-phenylhydrazone,
Z,E-1H-5-nitro-benz[g]indole-2,3-dione-3-phenylhydrazone,
E-5-nitro-1H-6,7,8,9-tetrahydro-benz[g]indole-2,3-dione-3-(2-nitrophenylhydrazone),
Z-1H-indole-2,3-dione-3-(2,4-dinitrophenylhydrazone),
Z-5,7-dinitro-1H-indole-2,3-dione-3-phenylhydrazone,
5-nitro-1H-6,7,8,9-tetrahydro-benz[g]indole-2,3-dione-3-phenylsulphonehydrazide,
5,9-dinitro-1H-benz[g]indole-2,3-dione-3-phenylsulphonehydrazide.

The quisqualate binding assay was performed as described by T. Honoré et al., Neuroscience Letters 54, 27–32 (1985).

The kainate binding assay was performed as described by T. Honoré et al., Neuroscience Letters 65, 47–52 (1986).

The glycine binding assay was performed as described by W. Frost White et al., Journal of Neurochemistry 53(2), 503-512 (1989).

Pharmaceutical Compositions

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) milligrams of active ingredients or, more broadly, 0.1 to one hundred (100) milligrams, per tablet, are accordingly suitable representative unit dosage forms.

Method of Treating

The compounds of this invention are extremely useful in the treatment of central nervous system disorders related to their biological activity. The compounds of this invention may accordingly be administered to a subject, including a human, in need of treatment, alleviation, or elimination of an indication associated with the biological activity of the compounds. This includes especially excitatory amino acid dependent psychosis, excitatory amino acid dependent anoxia, excitatory amino acid dependent ischemia, excitatory amino acid dependent convulsions and excitatory amino acid dependent migraine. Suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

Chemical Examples

Some compounds of the invention are old, and others are novel chemical entities. In any-way the compounds of the invention may be prepared according to chemical methods which are well known for a person skilled in the art.

EXAMPLE 1 a) 1-phenyl-1H-indole-2,3-dione

To a stirred solution of diphenylamine (3.2 g, 20 mmol) and 4-dimethylaminopyridine (10 mg) in chloroform (50 ml) was dropwise added oxalylchloride (3 ml). The resulting mixture was refluxed for 5 hours, whereafter it was cooled to room temperature and evaporated in vacuo.

The residue (oil) was redissolved in methylene chloride (50 ml) and dry $AlCl_3$ (3 g) was added. Stirring at room temperature was continued for 30 hours, whereafter ethanol (10 ml) followed by water (100 ml) were added. The organic phase was washed with saturated $Na_2CO_3$, dried over $Na_2SO_4$ and evaporated. The crystalline residue was stirred in ether (40 ml) and the product was filtered off. Yield: 2.65 g orange crystals, M.p. 139°-141° C., litt. 138° C.

b) The following 1-indole-2,3-diones were prepared according to known literature procedures.
[1] Organic Synthesis Col Vol. I p. 327.
[2] Martinet, J.: Compt. Rend. 166, 851, 1918.
4,6-ditrifluoromethyl-1H-indole-2,3-dione[1], M.p. 162°-165° C.
1H-benz[g]indole-2,3-dione[2], M.p. 242°-245° C.
7-trifluoromethyl-1H-indole-2,3-dione[1], M.p. 181°-183° C.
1H-6,7,8,9-tetrahydro-benz[g]indole-2,3-dione, M.p. 224°-226° C.
6-methoxy-1H-indole-2,3-dione, M.p. >310° C.
7-trifluoromethyl-1H-indole-2,3-dione, M.p. 180°-184° C.

c) 1-methyl-5-nitro-7-trifluoromethyl-1H-indole-2,3-dione

To a stirred 10° C. warm solution of KNO, (0.5 g) in 10 ml of conc. $H_2SO_4$ was dropwise added a solution of 1-methyl-7-trifluoromethyl-1H-indole-2,3-dione in 10 ml of conc. $H_2SO_4$. The addition was completed after 10 min, whereafter stirring was continued for 15 min at room temperature. The reaction mixture was poured on ice whereby the title compound precipitated as yellow crystals. The crystals were collected by filtration and washed with water. M.p. 168°-169° C.

In a similar manner to c), the following nitro compounds were prepared:
5-nitro-1H-6,7,8,9-tetrahydro-benz[g]indole-2,3-dione, M.p. 232°-236° C.
5-nitro-1-methyl-1H-benz[g]indole-2,3-dione, M.p. 255°-258° C.

d) 5,7-dinitro-1-methyl-1H-indole-2,3-dione

To a stirred solution of 5,7-dinitro-1H-indole-2,3-dione (1.2 g) in dry dimethylformamide (20 ml) was added sodium hydride (0.24 g 55% in mineral oil). After the hydrogen evolution had ceased methyl iodide (0.37 ml) was added. Stirring at room temperature was continued for 2 hours, whereafter the crude product was precipitated as an oil by addition of water (100 ml) to the reaction mixture. The oil crystallized upon treatment with ether/pentane, M.p. 154°-157° C.

In a similar manner to d), the following 1-alkyl- or 1-benzyl-1H-indole-2,3-diones were prepared.
5,7-dinitro-1-ethyl-1H-indole-2,3-dione, M.p. 135°-140° C.
5-bromo-1-methyl-1H-indole-2,3-dione, M.p. 157°-160° C.
1H-1-methyl-6,7,8,9-tetrahydro-benz[g]indole-2,3-dione, M.p. 157°-160° C.
5,7-dibromo-1-methyl-1H-indole-2,3-dione, M.p. 170°-173° C.
5,6-dichloro-1-methyl-1H-indole-2,3-dione, M.p. 180°-184° C.
4,5-dichloro-1-methyl-1H-indole-2,3-dione, M.p. 237°-239° C.
1-methyl-5-nitro-1H-indole-2,3-dione, M.p. 196°-199° C.
1-benzyl-5,7-dinitro-1H-indole-2,3-dione, M.p. 127°-131° C.
4,6-ditrifluoromethyl-1-methyl-1H-indole, M.p. 93°-94° C.

1-methyl-7-trifluoromethyl-1H-indole-2,3-dione, M.p. 120°–122° C.

6-methoxy-1-methyl-1H-indole-2,3-dione, M.p. 175°–178° C.

5,7-dinitro-1-(ethoxycarbonylmethyl)-1H-indole-2,3-dione, (oil).

1-methyl-1H-benz[g]indole-2,3-dione, M.p. 122°–126° C.

1-(ethoxycarbonylmethyl)-1H-indole-2,3-dione, M.p. 115°–119° C.

5,7-dibromo-1-(ethoxycarbonylmethyl)-1H-indole-2,3-dione, M.p. 97°–102° C.

1-methyl-1H-6,7,8,9-tetrahydrobenz[g]indole-2,3-dione, M.p. 160°–165° C.

e) 5-dimethylsulfamoyl-1H-indole-2,3-dione 10 g (68 mmol) isatin was added to 30 ml of chlorosulfonic acid at 30° C. for 30 minutes and was thereafter poured dropwise onto ice. A crude material was obtained (14.5 g). 7 g of this crude material was added to dimethylamine in water and ethyl acetate. This reaction mixture was stirred at RT for 1 hour and the organic phase was evaporated to yield and oil which was stirred with 1N hydrochloric acid in hot ethyl acetate. This mixture was extracted with ethyl acetate, which was evaporated in vacuo. The residue was recrystallized from ethanol. Yield of the title compound 550 mg, M.p. 265°–266° C.

In a similar manner the following compounds were prepared:
5-sulfamoyl-1H-6,7,8,9-tetrahydro-benz[g]indole-2,3-dione, M.p. >350° C.

EXAMPLE 2

E-5-nitro-1H-6,7,8,9-tetrahydro-benz[g]indole-2,3-dione-3-(2-nitrophenylhydrazone)

0.5 g (2 mmol) of 5-nitro-1H-6,7,8,9-tetrahydro-benz[g]indole-2,3-dione, 0.34 g (2.2 mmol) 2-nitrophenylhydrazin and 2 drops of 1N HCl were dissolved in 15 ml of methanol and the mixture was stirred at room temperature for 30 minutes. The precipitate was isolated by filtration. The crude reaction product consisted of a mixture of the two isomers (Z and E forms) of the title compound. The title compound was obtained by washing the crude reaction product with tetrahydrofuran (THF) due to different solubility of the E and Z isomer in THF. Yield 350 mg of the title compound. M.p. >350° C.

In similar way the following compounds were prepared from the appropriate isatine and hydrazine or sulphonehydrazide compounds. The Z and E isomers were obtained by utilizing their different solubility in THF. Furthermore an E isomer may be transformed into a Z isomer by heating in THF.

Z,E-1H-6,7,8,9-tetrahydro-benz[g]indole-2,3-dione-3-phenylhydrazone, M.p. 288°–290° C.

E-1H-5,7-dinitro-1-methyl-indole-2,3-dione-3-(2-nitrophenylhydrazone), M.p. 320°–321° C.

Z-1-phenyl-1H-indole-2,3-dione-3-(2-nitrophenylhydrazone), M.p. 191°–194° C.

E-1-phenyl-1H-indole-2,3-dione-3-(2-nitrophenylhydrazone), M.p. 206°–210° C.

Z/E-5-nitro-1H-benz[g]indole-2,3-dione-3-phenylhydrazone, M.p 294°–295° C.

Z-5-nitro-1H-indole-2,3-dione-3-phenylhydrazone, M.p. 279°–281° C.

Z-5,7-dinitro-1H-indole-2,3-dione-3-phenylhydrazone, M.p. 301°–302° C.

Z-1H-indole-2,3-dione-3-(2,4-dinitrophenylhydrazone), M.p. 344°–348° C.

Z-1H-indole-2,3-dione-3-phenylhydrazone, M.p. 203°–205° C.

E-1H-indole-2,3-dione-3-(2-nitrophenylhydrazone), M.p. 288°–291° C.

5,9-dinitro-1H-benz[g]indole-2,3-dione-3-phenylsulphonylhydrazone, M.p. 144°–146° C.

5-nitro-1H-6,7,8,9-tetrahydro-benz[g]indole-2,3-dione-3-phenylsulphonylhydrazone, M.p. 173°–175° C.

5-nitro-1H-benz[g]indole-2,3-dione-3-phenylsulphonylhydrazone, M.p. 195°–198° C.

5,7-dinitro-1H-indole-2,3-dione-3-phenylsulphonylhydrazone, M.p. 200°–202° C.

EXAMPLE 3

The following compounds as E, Z or E/Z isomers are prepared according to the same procedure as given in example 2 by combinations of different isatin derivatives and hydrazines.

5-nitro-1H-6,7,8,9-tetrahydro-benz[g]indole-2,3-dione-3-(2-pyridylhydrazone), 5-nitro-1H-6,7,8,9-tetrahydro-benz[g]indole-2,3-dione-3-(4-fluorophenylhydrazone), 1H-5,7-dinitro-indole-2,3-dione-3-(4-sulfamoylphenylhydrazone), 7-$CF_3$-1H-indole-2,3-dione-3-(2-nitrophenylhydrazone), 4,6-ditrifluoromethyl-1H-indole-2,3-dione-3-(2-nitrophenylhydrazone), 1-methyl-5-nitro-7-trifluoromethyl-1H-2,3-dione-3-(2-nitrophenylhydrazone), 5,6-dicloro-1-methyl-1H-indole-2,3-dione-3-(2-pyridylhydrazone), 5-dimethylsulfamoyl-1H-indole-2,3-dione-3-(2-nitrophenylhydrazone), 7-sulfamoyl-8-nitro-benz[e]indole-2,3-dione-3-(2-nitrophenylhydrazone), 8-nitro-4,5,6,7-tetrahydro-benz[e]indole-2,3-dione-3-(2-nitrophenylhydrazone), 7-sulfamoyl-8-nitro-benz[e]indole-2,3-dione-3-phenylsulphonylhydrazone, 8-sulfamoyl-4,5,6,7-tetrahydro-benz[e]indole-2,3-dione-3-phenylsulphonylhydrazone.

It is thus seen that the present invention provides a new and convenient process for the production of indole-2,3-dione-3-hydrazone compounds, certain novel indole-2,3-dione-3-hydrazone compounds which are useful as excitatory amino acid antagonists, pharmaceutical-compositions useful as excitatory amino acid antagonists comprising certain indole-2,3-dione-3-hydrazone compounds, and a method of antagonizing the biological effects of excitatory amino acids in a subject in need thereof comprising the step of administering certain indole-2,3-dione-3-hydrazone compounds or a pharmaceutical composition comprising the same together with a pharmaceutically-acceptable diluent or carrier, all having the foregoing characteristics and advantages.

It is to be understood that the invention is not to be limited to the exact details of operation, or to the exact methods, procedures, or embodiments shown and described, as obvious modifications and equivalents will be apparent to one skilled in the art, and the invention is therefore to be limited only by the full scope of the appended claims.

We claim:

1. A method of antagonizing the biological effects of an excitatory amino acid of a subject in need of such antagonization comprising the step of administering to said subject an effective excitatory amino acid antagonizing amount of an indole-2,3-dione-3-hydrazone compound having the formula

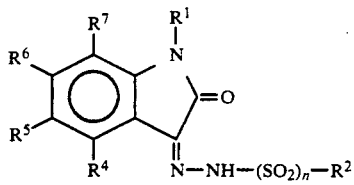

wherein
n is 0 or 1;
$R^1$ is hydrogen, $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein R' is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;
$R^2$ is pyridyl or phenyl, both of which may be substituted one or more times preferably in the ortho and para positions with halogen, $CF_3$, $NO_2$, $CN$, phenyl, or $SO_2NR''R'''$ wherein R'' and R''' independently are hydrogen, benzyl, or $C_{1-6}$-alkyl;
$R^4$, $R^5$, $R^6$, $R^7$ independently are hydrogen, $C_{1-6}$-alkyl which may be branched, phenyl, halogen, $C_{1-6}$-alkoxy, $NO_2$, $CN$, $CF_3$, or $SO_2NR^{11}R^{12}$ wherein $R^{11}$ and $R^{12}$ independently are hydrogen, benzyl, or $C_{1-6}$-alkyl; or $R^6$ and $R^7$ together form an additional 4 to 8 membered carbocyclic ring which may be aromatic or partial saturated and which may be substituted with halogen, $NO_2$, $CF_3$, $CN$, $SO_2NR^{13}R^{14}$ wherein $R^{13}$ and $R^{14}$ independently are hydrogen, benzyl, or $C_{1-6}$-alkyl, and $R^4$ and $R^5$ have the meanings set forth above;
or $R^4$ and $R^5$ together form an additional 4 to 8 membered carbocyclic ring which may be aromatic or partial saturated and which may be substituted with halogen, $NO_2$, $CF_3$, $CN$, $SO_2NR^{13}R^{14}$ wherein $R^{13}$ and $R^{14}$ independently are hydrogen, benzyl, or $C_{1-6}$-alkyl, and $R^6$ and $R^7$ have the meanings set forth above;

2. A method according to claim 1 wherein at least one of $R^4$, $R^5$, $R^6$ or $R^7$ is an electron withdrawing substituent selected from the group consisting of $NO_2$, $CF_3$, $CN$, $SO_2NR^{11}R^{12}$, and halogen and $R^1$, $R^2$, $R^4$, $R^5$, $R^6$, $R^7$, $R^{11}$, and $R^{12}$ otherwise have the meanings set forth in claim 1.

3. A method according to claim 1 wherein $R^5$ is $NO_2$, F, $CF_3$, or CN.

4. A method of antagonizing the biological effects of an excitatory amino acid according to claim 1, wherein the compound is administered in the form of a pharmaceutical composition thereof, in which it is present together with a pharmaceutically acceptable carrier or diluent.

5. A method of antagonizing the biological effects of an excitatory amino acid according to claim 2, wherein the compound is administered in the form of a pharmaceutical composition thereof, in which it is present together with a pharmaceutically acceptable carrier or diluent.

6. A pharmaceutical composition for use in antagonizing the biological effects of an excitatory amino acid of a subject in need of such antagonization comprising an effective excitatory amino acid antagonizing amount of a tricyclic compound having the formula

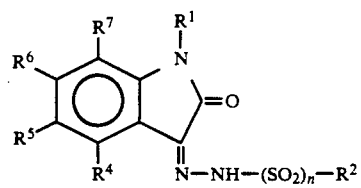

wherein
n is 0 or 1;
$R^1$ is hydrogen, $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein R' is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;
$R^2$ is pyridyl or phenyl, both of which may be substituted one or more times preferably in the ortho and para positions with halogen, $CF_3$, $NO_2$, $CN$, phenyl, or $SO_2NR''R'''$ wherein R'' and R''' independently are hydrogen, benzyl, or $C_{1-6}$-alkyl;
$R^4$, $R^5$ independently are hydrogen, $C_{1-6}$-alkyl which may be branched, phenyl, halogen, $C_{1-6}$-alkoxy, $NO_2$, $CN$, $CF_3$, or $SO_2NR^{11}R^{12}$ wherein $R^{11}$ and $R^{12}$ independently are hydrogen, benzyl, or $C_{1-6}$-alkyl; And $R^6$ and $R^7$ together form an additional 4 to 8 membered carbocyclic ring which may be aromatic or partial saturated and which may be substituted with halogen, $NO_2$, $CF_3$, $CN$, $SO_2NR^{13}R^{14}$ wherein $R^{13}$ and $R^{14}$ independently are hydrogen, benzyl, or $C_{1-6}$-alkyl; Or $R^6$, $R^7$ independently are hydrogen, $C_{1-6}$-alkyl which may be branched, phenyl, halogen, $C_{1-6}$-alkoxy, $NO_2$, $CN$, $CF_3$, or $SO_2NR^{11}R^{12}$ wherein $R^{11}$ and $R^{12}$ independently are hydrogen, benzyl, or $C_{1-6}$-alkyl; And $R^4$ and $R^5$ together form an additional 4 to 8 membered carbocyclic ring which may be aromatic or partial saturated and which may be substituted with halogen, $NO_2$, $CF_3$, $CN$, $SO_2NR^{13}R^{14}$ wherein $R^{13}$ and $R^{14}$ independently are hydrogen, benzyl, or $C_{1-6}$-alkyl;
provided that $R^1$, $R^4$ and $R^5$ are not all hydrogen when $R^2$ is unsubstituted phenyl and $R^6$ and $R^7$ together form an additional unsubstituted benzo ring.

7. A method of antagonizing the biological effects of an excitatory amino acid of a subject in need thereof comprising the step of administering to said subject a pharmaceutical composition according to claim 6.

8. A tricyclic compound having the formula

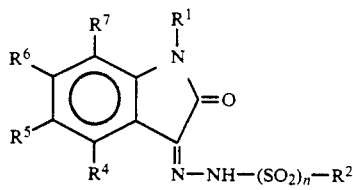

wherein n is 0 or 1;

$R^1$ is hydrogen, $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;

$R^2$ is pyridyl or phenyl, both of which may be substituted one or more times preferably in the ortho and para positions with halogen, $CF_3$, $NO_2$, CN, phenyl, or $SO_2NR''R'''$ wherein $R''$ and $R'''$ independently are hydrogen, benzyl, or $C_{1-6}$-alkyl;

$R^4$, $R^5$ independently are hydrogen, $C_{1-6}$-alkyl which may be branched, phenyl, halogen, $C_{1-6}$-alkoxy, $NO_2$, CN, $CF_3$, or $SO_2NR^{11}R^{12}$ wherein $R^{11}$ and $R^{12}$ independently are hydrogen, benzyl, or $C_{1-6}$-alkyl; And $R^6$ and $R^7$ together form an additional 4 to 8 membered carbocyclic ring which may be aromatic or partial saturated and which may be substituted with halogen, $NO_2$, $CF_3$, CN, $SO_2NR^{13}R^{14}$ wherein $R^{13}$ and $R^{14}$ independently are hydrogen, benzyl, or $C_{1-6}$-alkyl; Or $R^6$, $R^7$ independently are hydrogen, $C_{1-6}$-alkyl which may be branched, phenyl, halogen, $C_{1-6}$-alkoxy, $NO_2$, CN, $CF_3$, or $SO_2NR^{11}R^{12}$ wherein $R^{11}$ and $R^{12}$ independently are hydrogen, benzyl, or $C_{1-6}$-alkyl; And $R^4$ and $R^5$ together form an additional 4 to 8 membered carbocyclic ring which may be aromatic or partial saturated and which may be substituted with halogen, $NO_2$, $CF_3$, CN, $SO_2NR^{13}R^{14}$ wherein $R^{13}$ and $R^{14}$ independently are hydrogen, benzyl, or $C_{1-6}$-alkyl;

provided that $R^1$, $R^4$ and $R^5$ are not all hydrogen when $R^2$ is unsubstituted phenyl and $R^6$ and $R^7$ together form an additional unsubstituted benzo ring.

9. A compound according to claim 8 wherein the additional ring formed by $R^6$ and $R^7$ or $R^4$ and $R^5$ is substituted with halogen, $NO_2$, $CF_3$, CN or $SO_2NR^{13}R^{14}$ wherein $R^{13}$ and $R^{14}$ independently are hydrogen, benzyl, or $C_{1-6}$-alkyl.

10. A compound of claim 8, which is 8-nitro-1H-4,5,6,7-tetrahydro-benz[e]indole-2,3-dione-3-(2-nitrophenylhydrazone.

11. A compound of claim 8, which is 5-nitro-1H-6,7,8,9-tetrahydro-benz[g]indole-2,3-dione-3-phenylsulphonylhydrazone.

12. A compound of claim 8, which is 5-nitro-1H-6,7,8,9-tetrahydro-benz[g]indole-2,3-dione-3-(2-pyridylhydrazone).

* * * * *